United States Patent [19]
Kastman et al.

[11] Patent Number: 6,092,002
[45] Date of Patent: *Jul. 18, 2000

[54] VARIABLE TENSION PROCESS AND APPARATUS FOR CONTINUOUSLY MOVING LAYERS

[75] Inventors: Scott Lee Kastman, Greenville; Robert Griffiths Brandon; Louis Maurice Chapdelaine, both of Appleton; Joseph Daniel Coenen, Neenah; Robert Lee Popp, Hortonville; Devertt DeWayne Woolwine, Neenah, all of Wis.

[73] Assignee: Kimberly-Clark Worldwide, Inc., Neenah, Wis.

[ * ] Notice: This patent is subject to a terminal disclaimer.

[21] Appl. No.: 08/949,404

[22] Filed: Oct. 14, 1997

Related U.S. Application Data

[60] Provisional application No. 60/030,684, Nov. 13, 1996, and provisional application No. 60/057,279, Aug. 29, 1997.

[51] Int. Cl.[7] ............................... G06F 19/00; B23B 31/00
[52] U.S. Cl. ........................ 700/118; 700/131; 700/125; 156/229
[58] Field of Search .................................. 700/117, 131, 700/132, 137; 156/164, 204

[56] References Cited

U.S. PATENT DOCUMENTS

| | | | |
|---|---|---|---|
| 2,682,909 | 7/1954 | Claff et al. | 154/1.7 |
| 2,990,173 | 6/1961 | Melville | 270/52 |
| 3,004,880 | 10/1961 | Lord | 156/64 |
| 3,127,292 | 3/1964 | Early | 156/64 |
| 3,276,183 | 10/1966 | Carlisle, Jr. et al. | 53/51 |
| 3,294,301 | 12/1966 | Richter | 226/27 |
| 3,326,436 | 6/1967 | Huck | 226/25 |
| 3,559,568 | 2/1971 | Stanley | 101/32 |
| 3,589,095 | 6/1971 | James et al. | 53/51 |
| 3,762,125 | 10/1973 | Prena | 53/51 |
| 3,806,390 | 4/1974 | Balk et al. | 156/229 |
| 3,811,987 | 5/1974 | Wilkinson et al. | 156/497 |
| 3,887,419 | 6/1975 | Geschwender | 156/197 |
| 3,978,637 | 9/1976 | Mauriello | 53/28 |
| 4,007,866 | 2/1977 | Traise | 226/31 |
| 4,018,028 | 4/1977 | Donnet | 53/51 |
| 4,070,226 | 1/1978 | Crathern et al. | 156/364 |
| 4,129,238 | 12/1978 | Herd | 226/29 |
| 4,135,664 | 1/1979 | Resh | 235/475 |
| 4,239,570 | 12/1980 | Kerwin | 156/163 |
| 4,248,655 | 2/1981 | Kerwin | 156/351 |
| 4,254,173 | 3/1981 | Peer, Jr. | 428/204 |
| 4,295,912 | 10/1981 | Burns | 156/324 |

(List continued on next page.)

FOREIGN PATENT DOCUMENTS

| | | | |
|---|---|---|---|
| 0 009 739 A2 | 4/1980 | Canada | B65C 3/16 |
| 1158537 | 12/1983 | Canada | B65B 41/18 |
| 1163548 | 3/1984 | Canada | B65B 41/18 |
| 1253062 | 4/1989 | Canada | B32B 31/08 |
| 20165429 A1 | 11/1990 | Canada | B32B 3/00 |
| 1283814 | 5/1991 | Canada | A61F 13/15 |

(List continued on next page.)

OTHER PUBLICATIONS

Patent Abstracts of Japan 58–220,039: Description of Nakamura Ko et al., "Material Feeding Control System."

*Primary Examiner*—William Grant
*Assistant Examiner*—Kidesi Bahta
*Attorney, Agent, or Firm*—Thomas M. Gage; Douglas L. Miller

[57] ABSTRACT

A process and apparatus for controllably registering two continuously moving layers of material is provided. A continuously moving first layer has a plurality of components, and a continuously moving second layer has a plurality of reference marks representing a respective plurality of components. The process and apparatus control the distance between reference marks of the second layer to a selected distance, and then controllably registers each reference mark of the second layer to a respective component of the continuously moving first layer.

24 Claims, 7 Drawing Sheets

U.S. PATENT DOCUMENTS

| | | | |
|---|---|---|---|
| 4,315,508 | 2/1982 | Bolick | 604/392 |
| 4,316,566 | 2/1982 | Arleth et al. | 226/2 |
| 4,322,026 | 3/1982 | Young, Jr. | 226/15 |
| 4,349,997 | 9/1982 | Hayasaka et al. | 53/51 |
| 4,392,910 | 7/1983 | Tokuno et al. | 156/361 |
| 4,397,704 | 8/1983 | Frick | 156/201 |
| 4,397,709 | 8/1983 | Schwenzer | 156/351 |
| 4,400,230 | 8/1983 | Wyslotsky | 156/361 |
| 4,417,935 | 11/1983 | Spencer | 156/80 |
| 4,425,173 | 1/1984 | Frick | 156/204 |
| 4,496,417 | 1/1985 | Haake et al. | 156/361 |
| 4,543,141 | 9/1985 | Bradley et al. | 156/164 |
| 4,549,917 | 10/1985 | Jensen, Jr. | 156/108 |
| 4,572,752 | 2/1986 | Jensen et al. | 156/64 |
| 4,576,663 | 3/1986 | Bory | 156/64 |
| 4,610,739 | 9/1986 | Jensen | 156/64 |
| 4,615,695 | 10/1986 | Cooper | 604/385 A |
| 4,704,171 | 11/1987 | Thompson et al. | 156/64 |
| 4,711,683 | 12/1987 | Merkatoris | 156/164 |
| 4,720,415 | 1/1988 | Vander Wielen et al. | 428/152 |
| 4,795,513 | 1/1989 | Jensen, Jr. | 156/108 |
| 4,819,406 | 4/1989 | Redmond | 53/51 |
| 4,837,715 | 6/1989 | Ungpiyakul et al. | 364/552 |
| 4,883,549 | 11/1989 | Frost et al. | 156/161 |
| 4,888,717 | 12/1989 | Ditto et al. | 364/559 |
| 4,909,879 | 3/1990 | Ball | 156/164 |
| 4,935,087 | 6/1990 | GIlman | 156/251 |
| 4,940,464 | 7/1990 | Van Gompel et al. | 604/396 |
| 5,045,135 | 9/1991 | Meissner et al. | 156/64 |
| 5,046,272 | 9/1991 | Vogt et al. | 38/143 |
| 5,094,708 | 3/1992 | Bechtel et al. | 156/351 |
| 5,104,116 | 4/1992 | Pohjola | 271/185 |
| 5,162,066 | 11/1992 | Martensson et al. | 156/163 |
| 5,185,055 | 2/1993 | Temple et al. | 156/630 |
| 5,200,020 | 4/1993 | Collins et al. | 156/520 |
| 5,221,058 | 6/1993 | Fillis | 242/57.1 |
| 5,224,405 | 7/1993 | Pohjola | 83/24 |
| 5,235,515 | 8/1993 | Ungpiyakul et al. | 364/469 |
| 5,269,123 | 12/1993 | Marchesini | 53/559 |
| 5,304,272 | 4/1994 | Rohrbacker et al. | 156/209 |
| 5,359,525 | 10/1994 | Weyenberg | 364/469 |
| 5,366,791 | 11/1994 | Carr et al. | 428/195 |
| 5,383,988 | 1/1995 | Herrmann et al. | 156/64 |
| 5,389,093 | 2/1995 | Howell | 604/361 |
| 5,470,411 | 11/1995 | Gloton et al. | 156/64 |
| 5,483,893 | 1/1996 | Isaac et al. | 101/485 |
| 5,492,591 | 2/1996 | Herrmann et al. | 156/538 |
| 5,540,796 | 7/1996 | Fries | 156/164 |
| 5,575,782 | 11/1996 | Hasse et al. | 604/385.1 |
| 5,591,152 | 1/1997 | Buell et al. | 604/385.2 |
| 5,766,389 | 6/1998 | Brandon et al. | 156/64 |
| 5,818,719 | 10/1998 | Brandon et al. | 700/125 |
| B1 4,662,875 | 4/1989 | Hirotsu et al. | 604/389 |

FOREIGN PATENT DOCUMENTS

| | | | |
|---|---|---|---|
| 1287295 | 8/1991 | Canada | B65B 9/04 |
| 2044792 A1 | 5/1992 | Canada | G05D 5/04 |
| 2115455 A1 | 3/1993 | Canada | E04C 2/24 |
| 2121140 A1 | 4/1993 | Canada | B32B 3/00 |
| 2084837 A1 | 6/1993 | Canada | B32B 3/10 |
| 1336256 | 7/1995 | Canada | B32B 31/18 |
| 0 011 967 A1 | 6/1980 | European Pat. Off. | B65C 9/42 |
| 0 148 115 A1 | 7/1985 | European Pat. Off. | A41B 13/02 |
| 0 547 497 A2 | 6/1993 | European Pat. Off. | A61F 13/15 |
| 0 589 859 A1 | 3/1994 | European Pat. Off. | A61F 13/15 |
| 0 737 638 A1 | 10/1996 | European Pat. Off. | |
| 2 559 037 | 8/1985 | France | A41B 13/02 |
| 58-201611 | 11/1983 | Japan | B29C 27/00 |
| 63-5927 | 1/1988 | Japan | B29C 65/48 |
| 2 170 486 | 8/1986 | United Kingdom | |
| WO 88/03089 A1 | 5/1988 | WIPO | |
| WO 90/11886 A1 | 10/1990 | WIPO | B31F 1/20 |
| WO 90/11887 A1 | 10/1990 | WIPO | B31F 1/28 |
| WO 94/08789 A1 | 4/1994 | WIPO | |
| WO 95/18590 A2 | 7/1995 | WIPO | A61F 13/15 |
| WO 97/24094 A1 | 7/1997 | WIPO | |
| WO 97/24283 A1 | 7/1997 | WIPO | |

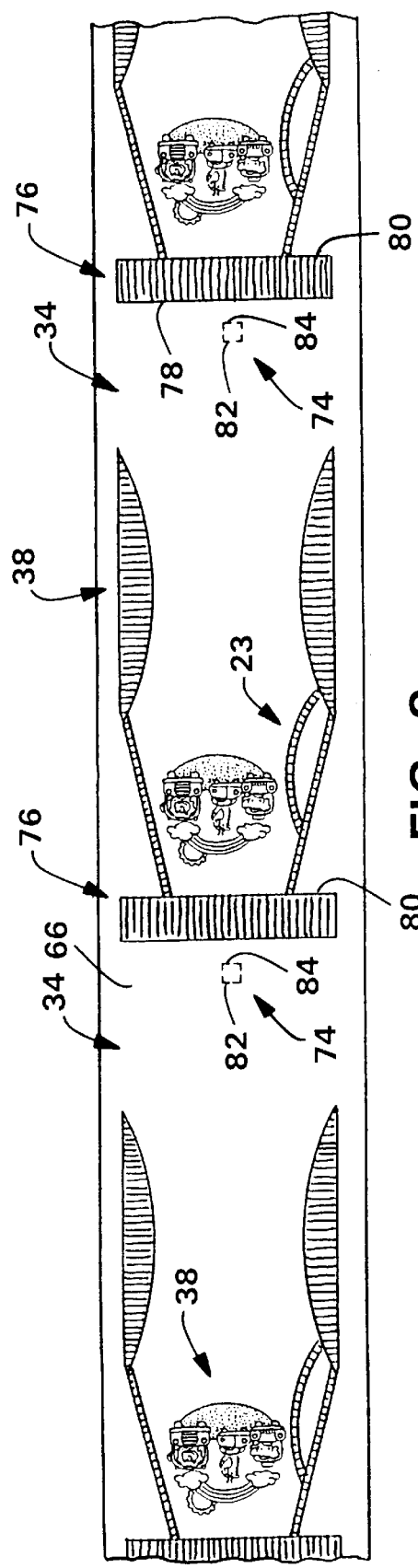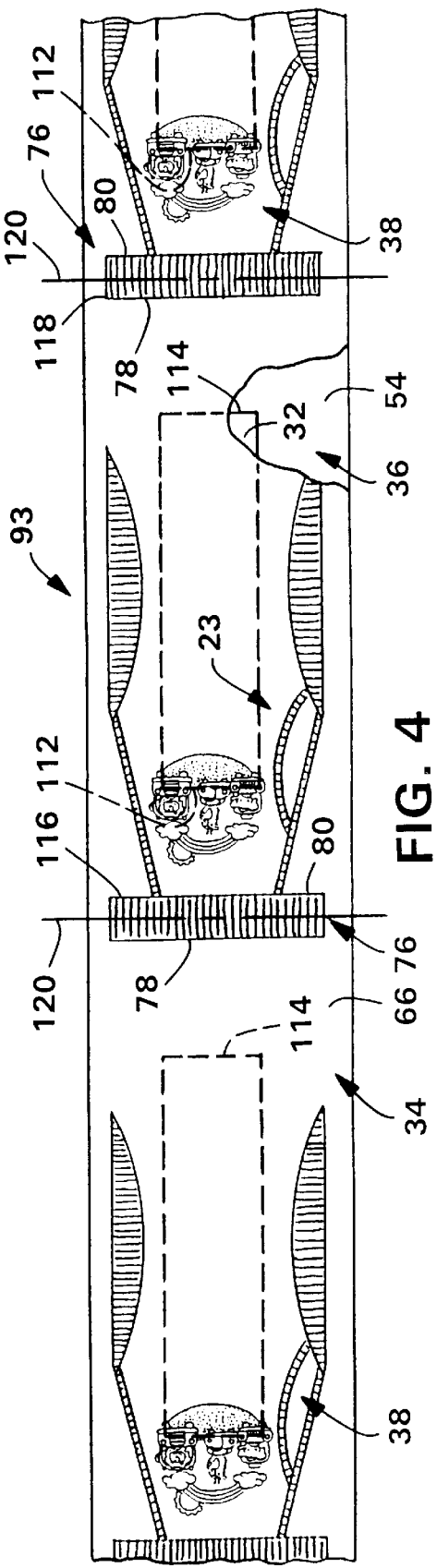

VARIABLE TENSION PROCESS AND APPARATUS FOR CONTINUOUSLY MOVING LAYERS

This application claims priority from U.S. Provisional Application Ser. No. 60/030,684 filed on Nov. 13, 1996 and U.S. Provisional Application Ser. No. 60/057,279 filed on Aug. 29, 1997.

BACKGROUND OF THE INVENTION

The present invention generally relates to processes and apparatus for making disposable absorbent articles, and particularly to processes and apparatus for making disposable absorbent articles having registered components.

Various products are fabricated in a continuous production line by the sequential addition of components to previously supplied components. This is particularly advantageous when one or more of the components can be supplied in the form of a single continuous layer. For example, in the formation of disposable absorbent articles, such as training pants, diapers, incontinence articles, feminine care products, or the like, a layer is normally supplied at a point in the fabrication line in the form of a continuous roll, and absorbent pads, waist elastic bands, leg elastic bands, stretchable side panels, and/or other elements or components can be individually, separately supplied at different points in the fabrication line as discrete objects to that layer.

Various methods and apparatus are available for bringing these individual, separate components of a single product together so that the components in the composite product are in a desired relation with respect to each other. In bringing these individual, separate components properly together, various known methods and apparatus are used to note the position of a particular component, and then to adjust the placement of subsequent components in order to properly position them.

One problem with current methods and apparatus is that they do not provide an adequate means for registering two continuously moving layers, and particularly when one of the layers has a pre-printed or pre-positioned component or the like that is to be registered with a pre-printed or pre-positioned component or the like on the other of the layers during the manufacture of a plurality of products having a desired registration of components.

SUMMARY OF THE INVENTION

In response to the discussed difficulties and problems encountered in the prior art, the present invention provides a process and apparatus for registering a plurality of components on one continuously moving layer with a respective plurality of components on another continuously moving layer.

In one form of the invention, there is provided a process for controllably registering a plurality of components of a continuously moving first layer with a plurality of components on a continuously moving second layer, comprising the steps of (1) providing a continuously moving first layer including a plurality of components, (2) providing a continuously moving second layer including a plurality of components, (3) representing the components of one of the continuously moving layers with a respective plurality of reference marks, (4) sensing each of the reference marks and generating a reference mark signal in response thereto, (5) measuring the distance between two successive reference mark signals and generating a repeat corrective control signal in accordance with preprogrammed instructions, (6) selectively applying pressure to the continuously moving one layer in response to a generated repeat corrective control signal to adjust the distance between two successive reference marks, (7) superimposing the continuously moving first layer and the continuously moving second layer together, (8) sensing a reference mark and its corresponding component of the other layer and generating a placement corrective control signal in accordance with preprogrammed instructions, and (9) adjusting the speed of the continuously moving one layer in response to a generated placement corrective control signal to controllably register the reference mark on the continuously moving one layer with its corresponding component on the continuously moving other layer.

In another form of the present invention, there is provided a process for controllably registering a plurality of reference marks of a continuously moving first layer with a plurality of corresponding reference marks of a continuously moving second layer, comprising the steps of (1) providing a continuously moving first layer including a plurality of reference marks selectively positioned thereon, (2) providing a continuously moving second layer including a plurality of corresponding reference marks selectively positioned thereon, (3) sensing each of the reference marks of one of the continuously moving layers and generating a reference mark signal in response thereto, (4) measuring the distance between two successive reference mark signals and generating a repeat corrective control signal in accordance with preprogrammed instructions, (5) impressing the continuously moving one layer in response to a generated repeat corrective control signal, (6) superimposing the continuously moving layers together, (7) sensing a reference mark of the continuously moving one layer and its corresponding reference mark of the continuously moving other layer and generating a placement corrective control signal in accordance with preprogrammed instructions, and (8) adjusting the speed of the continuously moving one layer in response to a generated placement corrective control signal to controllably register a reference mark of the continuously moving one layer with its corresponding reference mark on the continuously moving other layer.

In still another form of the present invention, there is provided an apparatus for controllably registering a plurality of components of a continuously moving first layer with a plurality of components on a continuously moving second layer comprising (1) means for providing a continuously moving first layer including a plurality of components, (2) means for providing a continuously moving second layer including a plurality of components being represented with a respective plurality of reference marks, (3) means for sensing each of the reference marks and means for generating a reference mark signal in response thereto, (4) means for measuring the distance between two successive reference mark signals, and means for generating a repeat corrective control signal in accordance with preprogrammed instructions, (5) means for selectively applying pressure to the continuously moving one layer in response to a generated repeat corrective control signal to adjust the distance between two successive reference marks, (6) means for superimposing the continuously moving first layer and the continuously moving second layer together, (7) means for sensing a reference mark and its corresponding component of the first layer, and means for generating a placement corrective control signal in accordance with preprogrammed instructions, and (8) means for adjusting the speed of the continuously moving second layer in response to a generated placement corrective control signal to controllably register a reference mark on the continuously moving second layer with its corresponding component on the continuously moving first layer.

In yet another form of the present invention, there is provided an apparatus for controllably registering a plurality of reference marks of a continuously moving first layer with a plurality of corresponding reference marks of a continuously moving second layer, comprising (1) means for providing a continuously moving first layer including a plurality of reference marks selectively positioned thereon, (2) means for providing a continuously moving second layer including a plurality of corresponding reference marks selectively positioned thereon, (3) means for sensing each of the reference marks of one of the continuously moving layers, and means for generating a reference mark signal in response thereto, (4) means for measuring the distance between two successive reference mark signals, and means for generating a repeat corrective control signal in accordance with pre-programmed instructions, (5) means for impressing the continuously moving one layer in response to a generated repeat corrective control signal, (6) means for superimposing the continuously moving layers together, (7) means for sensing a reference mark of the continuously moving one layer and its corresponding reference mark of the continuously moving other layer, and means for generating a placement corrective control signal in accordance with pre-programmed instructions, and (8) means for adjusting the speed of the continuously moving one layer in response to a generated placement corrective control signal to controllably register a reference mark of the continuously moving one layer with its corresponding reference mark on the continuously moving other layer.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings wherein:

FIG. 3 illustrates a continuously moving layer having a plurality of separate and distinct graphics thereon;

FIG. 4 illustrates a continuously moving composite layer having a plurality of separate and distinct graphics thereon;

DETAILED DESCRIPTION

Figure 1:
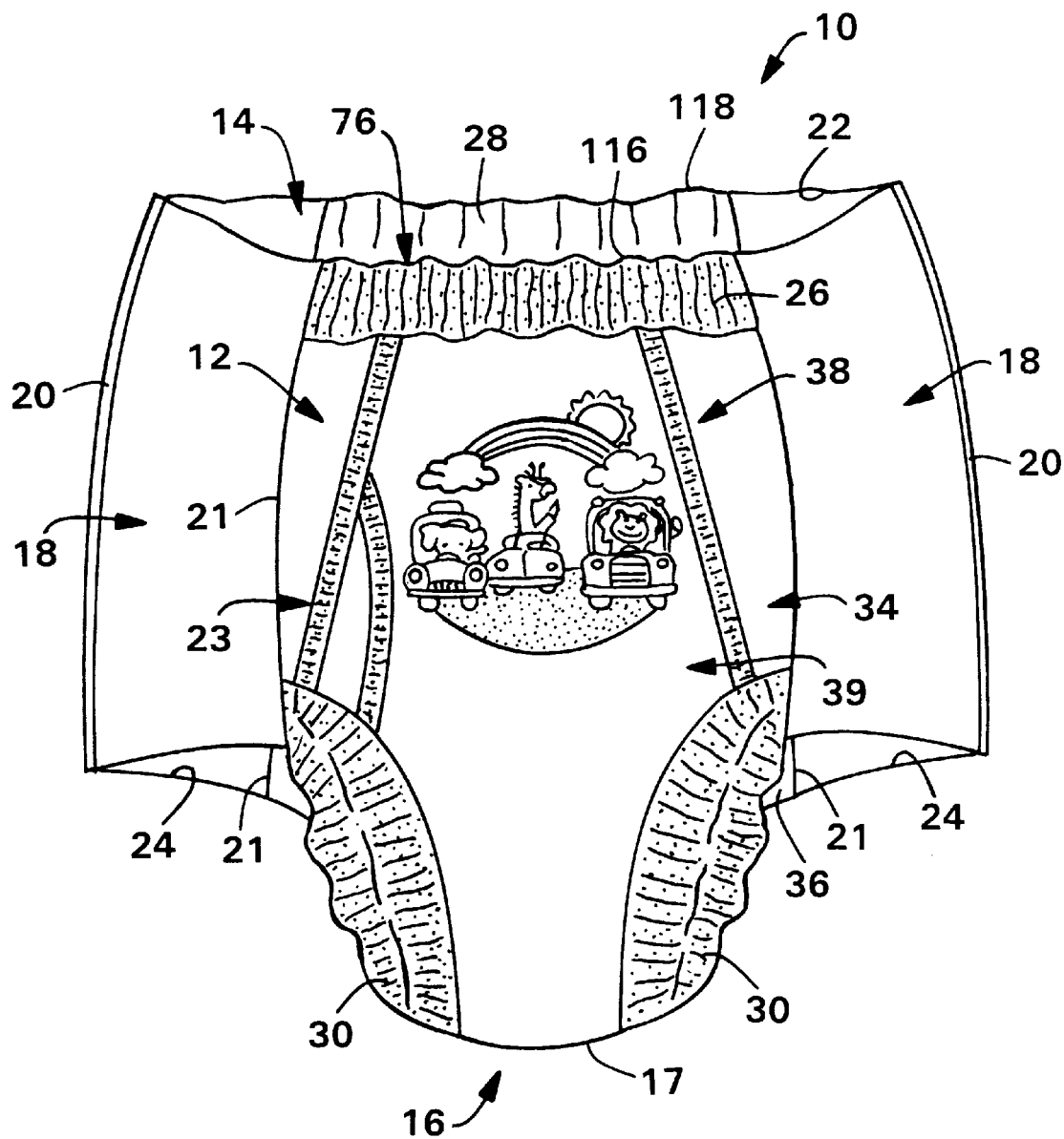
FIG. 1 illustrates a front view of one article having a registered graphic thereon.

The following detailed description will be made in the context of registering and controlling the registration of components on one continuously moving layer with components on at least a second continuously moving layer in the manufacture of disposable absorbent articles, and specifically a child's disposable absorbent training pant. Examples of other disposable absorbent articles include, but are not limited to, absorbent pants, diapers, feminine care products, incontinence products, or the like. The present invention also contemplates other products unrelated to disposable absorbent articles. For the purposes of this description, the term "product" can refer, but is not limited, to any article, device, laminate, composite, or the like. The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, or the like.

A child's disposable training pant can have, by way of example, multiple appearance-related and/or functional components registered within selected machine-direction (MD) and/or cross-direction (CD) ranges. The term "machine-direction" refers to the primary direction of movement of continuously moving layers in the manufacturing process, and the term "cross-direction" refers to a direction transverse to the machine-direction. The described example herein is that of registering a graphic in the machine direction within a designated area of the pant.

Thus, the present invention can provide a child's disposable training pant having one or more appearance-related or functional components registered with other components. Examples of components that are appearance-related include, but are not limited to, the registration of graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

Examples of functional components include, but are not limited to, waist elastics, leg elastics, areas of breatheability, fluid repellent areas, fluid wettable areas, adhesives or coatings, encapsulated inks, chemically-sensitive materials, environmentally-sensitive materials, heat-sensitive materials, moisture-sensitive materials, perfumes, odor control agents, inks, fasteners, fluid storage areas, textured or embossed areas, or the like.

The training pant described herein comprises an absorbent pad positioned between a liquid impermeable outer cover and a liquid permeable liner. The training pant further includes elastic side panels which are joined to the outer cover in order to provide elasticity thereto. The liquid impermeable outer cover can comprise two layers of material suitably joined together, in which the innermost layer can be a liquid impermeable layer and the outermost layer can be a nonwoven layer having cloth-like texture. In this case, it is the innermost liquid impermeable layer that has a graphic printed in registration thereon. The registered graphic generally includes a visually pleasing design or pattern and is controllably registered at a designated area in the product. An example of one registered graphic includes a graphic positioned on the front center of the pant, and includes a simulated elastic waistband, simulated elastic leg bands, a simulated "fly opening" for boys, simulated ruffles for girls, or the like. A more detailed description of the construction and design of a disposable absorbent training pant is in U.S. Pat. No. 4,940,464 issued Jul. 10, 1990, the contents of which are incorporated by reference herein.

Described herein is a distinctive process and apparatus for registering a plurality of distinct and separate components selectively positioned on a continuously moving first layer of material with a respective plurality of distinct and separate components selectively positioned on a continuously moving second layer of material. The second layer of material has the components suitably represented by or associated with respective reference marks, both provided thereon at a uniform repeat length that is the same, or substantially the same, as a machine product repeat length, defined hereafter. The distance between two successive reference marks is measured or determined, and then used to generate or calculate, if necessary, a repeat corrective control signal for the current process conditions. The repeat corrective control signal either will be a signal for elongating the layer, i.e., an elongating repeat corrective control signal, or a signal for gathering the layer, i.e., a gathering repeat corrective control signal. If a repeat corrective control signal is generated or calculated, the second layer of material is then controllably gathered or elongated so that the distance between two successive reference marks substantially equals the selected distance, which in this case is one machine product repeat length; this is termed the "repeat loop".

The second layer is controllably registered to the first layer of material so that each reference mark is selectively positioned or registered with a respective component of the first layer; this is termed the "placement loop", and the control signal generated is the placement corrective control signal. Even though the reference marks are preprinted on the layer so that any two successive reference marks are desirably a machine product repeat length apart, their distance apart can vary due to printing variations or errors, process conditions such as varying speeds, atmospheric conditions, variations in the material of which the layer is made, or the like. The repeat corrective control signal is combined with the placement corrective control signal. If the resultant corrective control signal is within acceptable tolerance and the two layers are registered together. If a resultant corrective control signal is outside acceptable tolerance, the second layer of material is then controllably gathered or elongated so that the two layers can be registered together. The term "reference mark" can refer, but is not limited, to components such as, by way of example, waist or leg elastics, adhesive beads, corners or edges or sides of structure; transporting mediums such as conveyor belts; visual marks, magnetic marks, electrical marks, electromagnetic marks, optical brighteners sensitive to ultraviolet radiation, or the like, all of which can be sensed, detected, or otherwise identified by an appropriate device. The term "machine product repeat length" refers to a selected distance, which in this example is the measured distance between successive, like components during manufacture. For example, between successive waist bands, absorbent pads, or the like. Or in other words, the machine product repeat length is the length of one product during the manufacturing process. Thus, when a reference mark is registered with a component of the first layer, then the component represented by that reference mark is registered with the component of the first layer.

With regard to the repeat loop, the second layer has the reference marks selectively provided thereon to correspond to a respective plurality of distinct and separate components, such as graphics. A first sensor generates a reference mark signal in response to each reference mark. The distance between each newly generated signal and the most recently preceding signal is suitably measured for an impressing mechanism or means, so that the mechanism or means can be operated, if necessary, to adjust the length between two successive reference marks by either gathering or elongating the second layer, so that the distance between a subsequent newly generated signal and its most recently preceding signal is one machine product repeat length. Thus, the repeat loop refers to repeatedly duplicating a product length between two successive reference marks.

The term "impressing", and variations thereof such as, by way of example, "impress", "impresser", "impression" or the like, refers generally to the selective application of pressure, for example, to a layer of material or layers of material. The amount of pressure can be applied selectively either to gather the layer or layers, or to elongate the layer or layers. Further, the area over which the pressure can be applied can be selected in any suitable manner. For example, the pressure can be applied across the full surface area, or of a portion only, of a layer or layers; can be applied as a single point, line, pattern, or the like; can be applied as a plurality of points, lines, patterns, or the like; or can be applied in any desirable combination of the above.

With regard to the placement loop, a desired registration of a reference mark to a component is performed by comparing and controlling a related datum value to a target set point. A "datum value" refers to a measured distance between a reference mark and a machine-generated constant reference signal. A "target set point" refers to a selected value within which the datum value is maintained.

There is described herein, by way of example, a distinctive process and apparatus for using a preprinted second layer of material including a plurality of distinct and separate graphics thereon, varying the length as necessary of the second layer to coincide with a selected length, and then applying and registering it to another layer that includes preassembled, preapplied components, such as absorbent pads, thereby providing a manufacturing process for individual disposable absorbent articles having graphics registered thereon at designated areas. The process and apparatus can also be used to apply, during manufacture, other various functional and appearance-related components that have been printed, joined, positioned, or the like, on a layer at a specified location so as to be selectively registered in the final product.

The second layer of material can be a continuous polyethylene film preprinted with a plurality of separate and distinct graphics. The printed graphics are arranged such that they ultimately will be positioned at the same designated area in each finished product. The term "finished" or "final", when used with reference to a product, means that the product has been suitably manufactured for its intended purpose.

The second layer is controllably gathered or elongated, when necessary, to appropriately coincide the distance between two successive reference marks to the machine product repeat length, and adjusted to control a related datum value to a target set point. This is done in order to register the reference marks to previously processed and preplaced components, such as, by way of example, absorbent pads. A system of sensors used in conjunction with computer hardware and software inspects for registered location, repeat patterns, and set point error. The data received from these sensors is used to control the manufacturing process as necessary for desired registration, so that the preprinted graphics are desirably registered with a respective plurality of components.

These features advantageously affect a layer moving at high speed in order to register it with another layer. In particular, there is provided accurate, real time information during the production process, and rapid adjustments to the process to provide the desired configuration and registration of the reference marks and their associated components in the final product. The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like.

Each of the separate and distinct graphics selectively positioned on the continuously moving layer is represented by or associated with a reference mark. This means that each reference mark is selectively positioned with regard to a respective graphic, so that the reference mark can be sensed and appropriately registered in the product, thereby properly registering each graphic in its product. Earlier, a reference mark was described in terms of specific examples, and in the following description the reference mark is selected as an optical brightener. A reference mark, whether an optical brightener or other means, can be configured in any desired size or shape. The reference mark may comprise a generally rectangular region having a machine direction dimension of about 19 millimeters and a cross direction dimension of about 37 millimeters. Other dimensions optionally may be employed. It is to be understood that the various detecting and sensing means described herein are to be appropriately compatible with the type of associated reference mark that is to be detected or sensed. The term "represented" or "associated" refers to the reference mark either being directly on a component that it represents, such as a graphic, or being selectively spaced therefrom. The optical brightener is provided to be sensitive to ultraviolet radiation. The optical brightener is, for example, capable of absorbing ultraviolet radiation and then fluorescing to emit light spectra that can be sensed by an appropriate and compatible detector or sensor. Ultraviolet radiation is generally understood to include electromagnetic radiation having wave lengths ranging from about 20–400 nanometers. Suitable optical brighteners include, for example, UVITEX OB manufactured by Ciba-Geigy, and LEUCOPURE EGM manufactured by Sandoz Chemicals Corporation.

Where the reference mark comprises ultraviolet sensitive optical brighteners, a suitable detector or sensor is a UV activated detector, such as a SICK detector model LUT 2-6 available from SICK OPTIK ELEKTRONIK, INC., a business having offices in St. Paul, Minn.

Other suitable reference marks, as well as sensors, computer devices, motors, and the like are described in U.S. Pat. No. 5,235,515; U.S. Pat. No. 5,359,525; and U.S. Pat. No. 4,837,715; the contents of these three aforementioned U.S. patents being incorporated by reference herein.

The described process and apparatus utilize several devices, and representative devices include encoders, signal counters, and sensors. An encoder generates a pulse train, which is a selected number of pulses per revolution of the encoder shaft, for subsequent counting and control. A signal counter receives a generated pulse train from an encoder, and counts the pulses for subsequent query. A sensor senses an occurrence or interruption in a process and generates a signal in response thereto.

Referring now to FIG. 1, there is illustrated a child's disposable training pant 10 generally comprising a front panel 12, a back panel 14, a crotch panel 16 interconnecting front and back panels 12, 14, and a pair of elastic side panels 18. Each elastic side panel 18 is formed from two separate elastic portions (FIG. 2A) and are suitably joined together, such as by ultrasonic bonding, to form a side seam 20. Upon the construction of side seams 20, a waist opening 22 and leg openings 24 are formed. The side seams 20 may be constructed to be manually tearable in order to allow training pant 10 to be disassembled manually by the caregiver, so that it can be easily removed from the child after a bowel movement. The elastic side panels 18 (FIG. 1) and side seams 20 can be provided in any suitable manner. One specific manner of supplying elastic side panels 18 is described in U.S. Pat. No. 5,224,405 and U.S. Pat. No. 5,104,116, both of which are incorporated by reference herein. The provision of side seams 20 can be accomplished in the manner described in U.S. Pat. No. 5,046,272, which is incorporated by reference herein.

Training pant 10 further comprises a front waist elastic 26 suitably joined to front panel 12, a back waist elastic 28 suitably joined to back panel 14, leg elastics 30 suitably joined to crotch panel 16, and an absorbent pad 32 (FIG. 4) positioned between a liquid impermeable outer cover or backsheet 34 (FIG. 1) and a liquid permeable liner or topsheet 36. The basic construction of a training pant is well known in the art, and one particular construction is that described in U.S. Pat. No. 4,940,464, issued Jul. 10, 1990, the contents of which are incorporated by reference herein. U.S. Pat. No. 4,940,464 also describes various materials of which a training pant can be made, and the methods of constructing the training pant.

As illustrated in FIG. 1, a registered graphic 38 is selectively positioned on front panel 12, and in this illustration comprises a design of a simulated "fly opening 23", typical of a boy's underwear, and a rainbow, sun, clouds, and cars. The registered graphic 38 can be any type of desired pattern, artistic feature, written instructions, or the like, and is desired to be positioned in the article at a selected location. Naturally, registered graphic 38 comprising a simulated fly opening 23 would be totally unacceptable from an aesthetic and/or functional viewpoint if it were located at crotch panel 16 or back panel 14.

Figure 2:
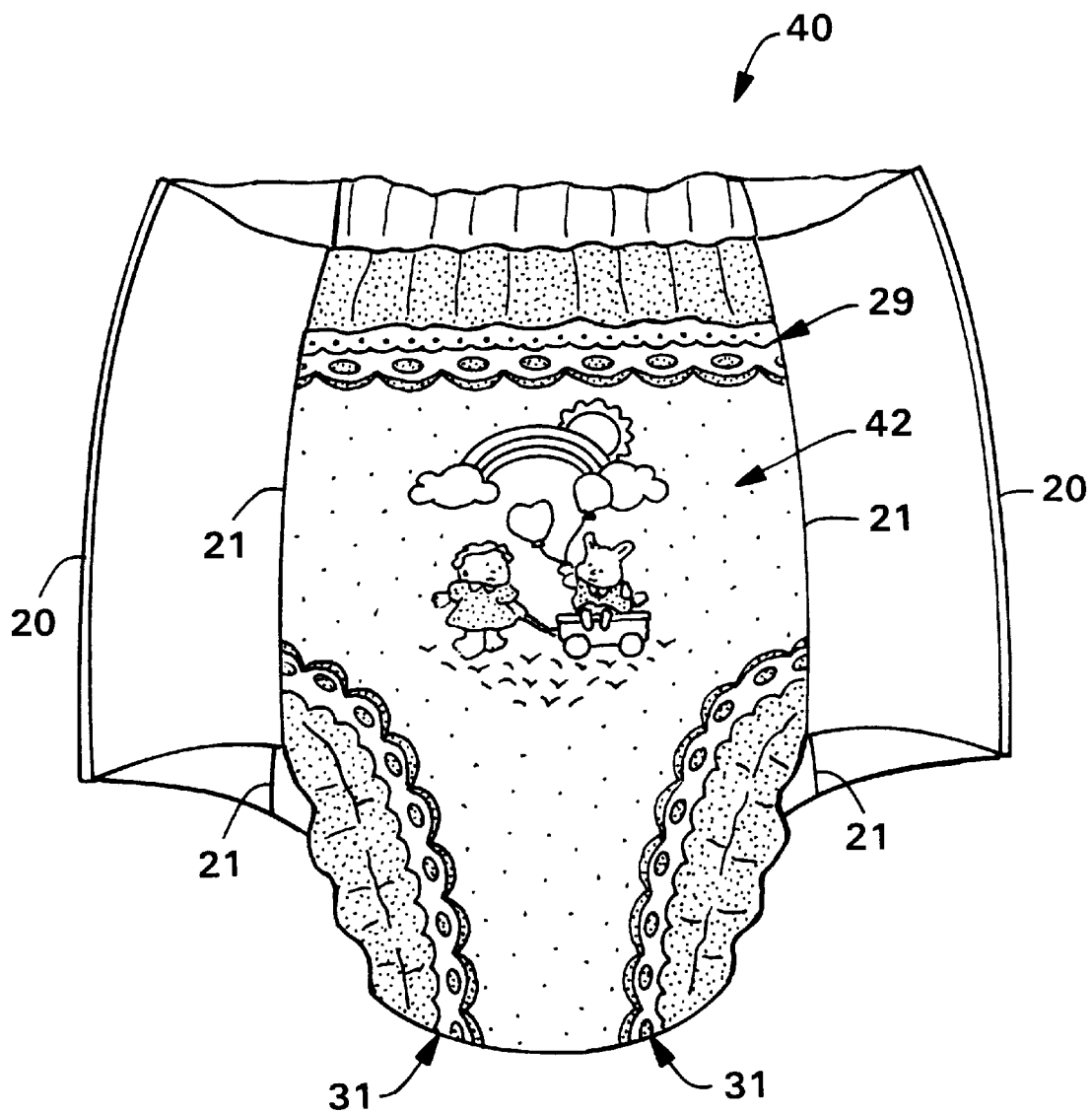
FIG. 2 illustrates a front view of another article having a registered graphic thereon.

Referring to FIG. 2, another training pant 40 is illustrated, which can be typically used for young girls. In this design, a registered graphic 42 includes simulated waist ruffles 29, simulated leg ruffles 31, a rainbow, sun, clouds, wagon and balloon. Again, any suitable design can be utilized for a training pant intended for use by young girls, so as to be aesthetically and/or functionally pleasing to them and the caregiver.

Registered graphic 38 in FIG. 1 or registered graphic 42 in FIG. 2 can be controllably registered as desired, depending upon the size and shape of the graphic and that portion of the article upon which the graphic is to be registered. In FIG. 1, graphic 38 is controllably registered within a designated area 39 which, as viewed in FIG. 1, is bounded or defined by a front waist edge 116, panel seams 21, and a crotch panel line 17. Panel seams 21 are the seams at which the respective elastic side panels 18 are suitably joined to front panel 12 and back panel 14. Again, a more specific description of the construction and manufacture of this design of a training pant 10 is contained in the aforementioned U.S. Pat. No. 4,940,464. The crotch panel line 17 is, for purposes of explanation herein, simply the line or boundary formed at the bottom of crotch panel 16 as illustrated in FIG. 1. Thus described, designated area 39 has four defined boundaries comprising front waist edge 116, panel seams 21, crotch panel line 17, and those portions of leg openings 24 extending between a respective panel seam 21 and crotch panel line 17. It is not necessary that a designated area 39 be completely defined or bounded by a closed line or closed boundary. For example, in FIG. 1, the designated area 39 could be defined by only front waist edge 116, panel seams 21, which sufficiently define a designated area 39 in which a graphic 38 can be controllably registered. In this case, the graphic 38 can be controllably registered a selected distance from front waist edge 116, and centered between panel seams 21.

Figure 2A:
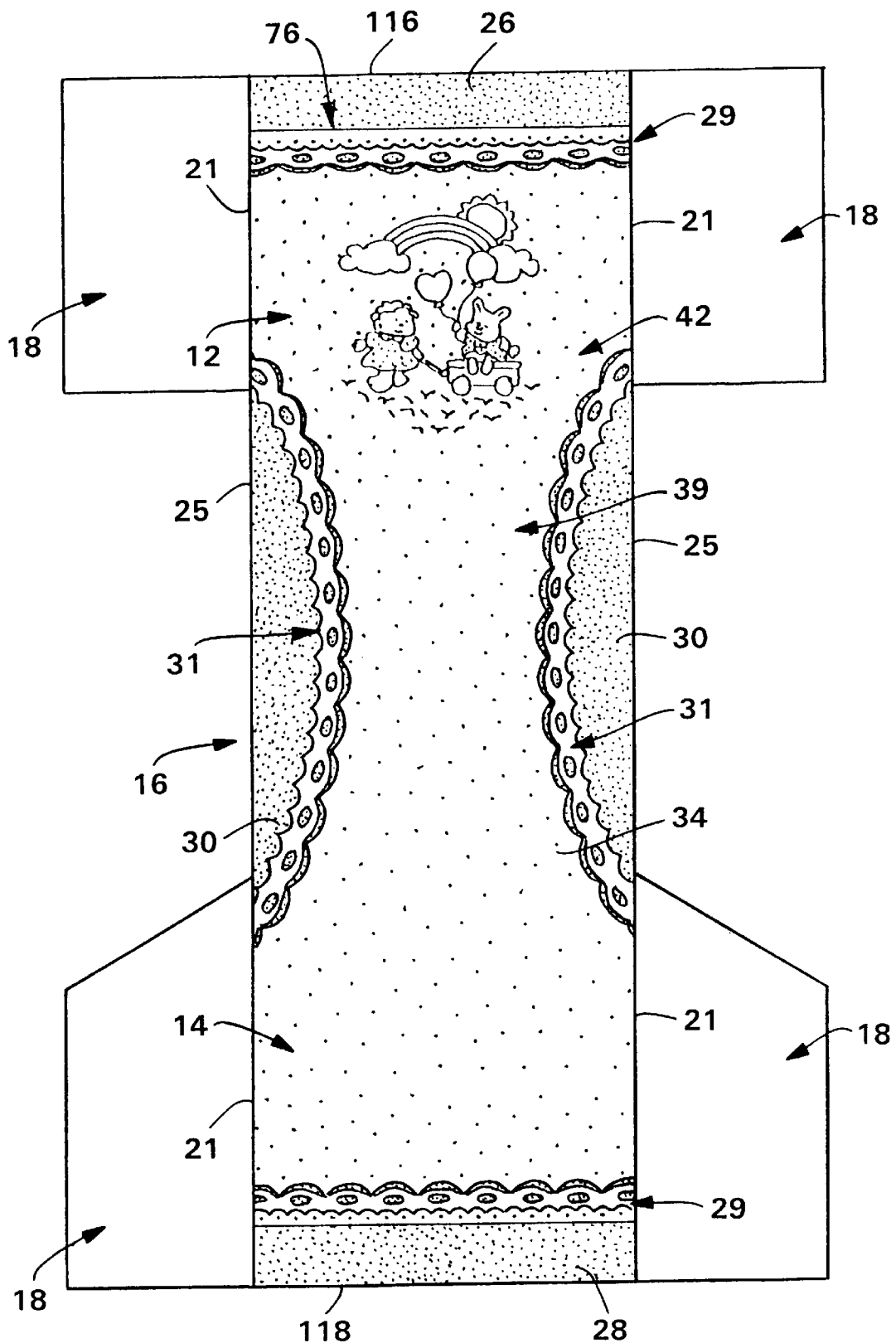
FIG. 2A representatively illustrates the article of FIG. 2 in a partially disassembled, stretched flat state.

Another example of the flexibility in choosing a designated area 39 is illustrated in FIG. 2A, which illustrates the training pant 40 in FIG. 2 in a partially disassembled, stretched flat state. This stretched flat state can be accomplished by taking the finished training pant 40 of FIG. 2 and manually tearing seams 20 and then laying the pant 40 flat and stretching it sufficiently to remove any gathers or pleating caused by any incorporated elastic members. In FIG. 2A, designated area 39 is defined or bounded by front waist edge 116, panel seams 21, back waist edge 118, and a pair of leg opening edges 25 extending between respective panel seams 21. Thus, in FIG. 2A, designated area 39 is generally rectangular in shape, and registered graphic 42 is registered within and throughout the surface area of designated area 39. Registered graphic 42 comprises several component designs, such as simulated leg ruffles 31 and simulated waist ruffles 29. As viewed in FIG. 2A, leg opening edges 25 are linear or straight lines. However, in FIG. 2, simulated leg ruffles 31 provide a perceived curvature or shape to training pant 40, which is one of the unique features herein.

There is uniquely and advantageously provided a very close tolerance in the registration of a desired component, such as graphics 38, 42, within any selected area, such as a designated area 39. With reference to FIG. 1, it is apparent that the simulated fly opening 23 of graphic 38 needs to be registered within front panel 12. It would be undesirable to have training pant 10 manufactured by a method and/or apparatus that could not control the proper registration of simulated fly opening 23, otherwise the simulated fly opening 23 could appear at back panel 14 or crotch panel 16. The present invention provides a highly controlled registration of a desired component, such as a graphic 38 or 42, within a desired designated area, such as designated area 39 within a tolerance of about plus or minus 12 millimeters, and within a more particular tolerance between about plus or minus 3 millimeters.

Figure 5:
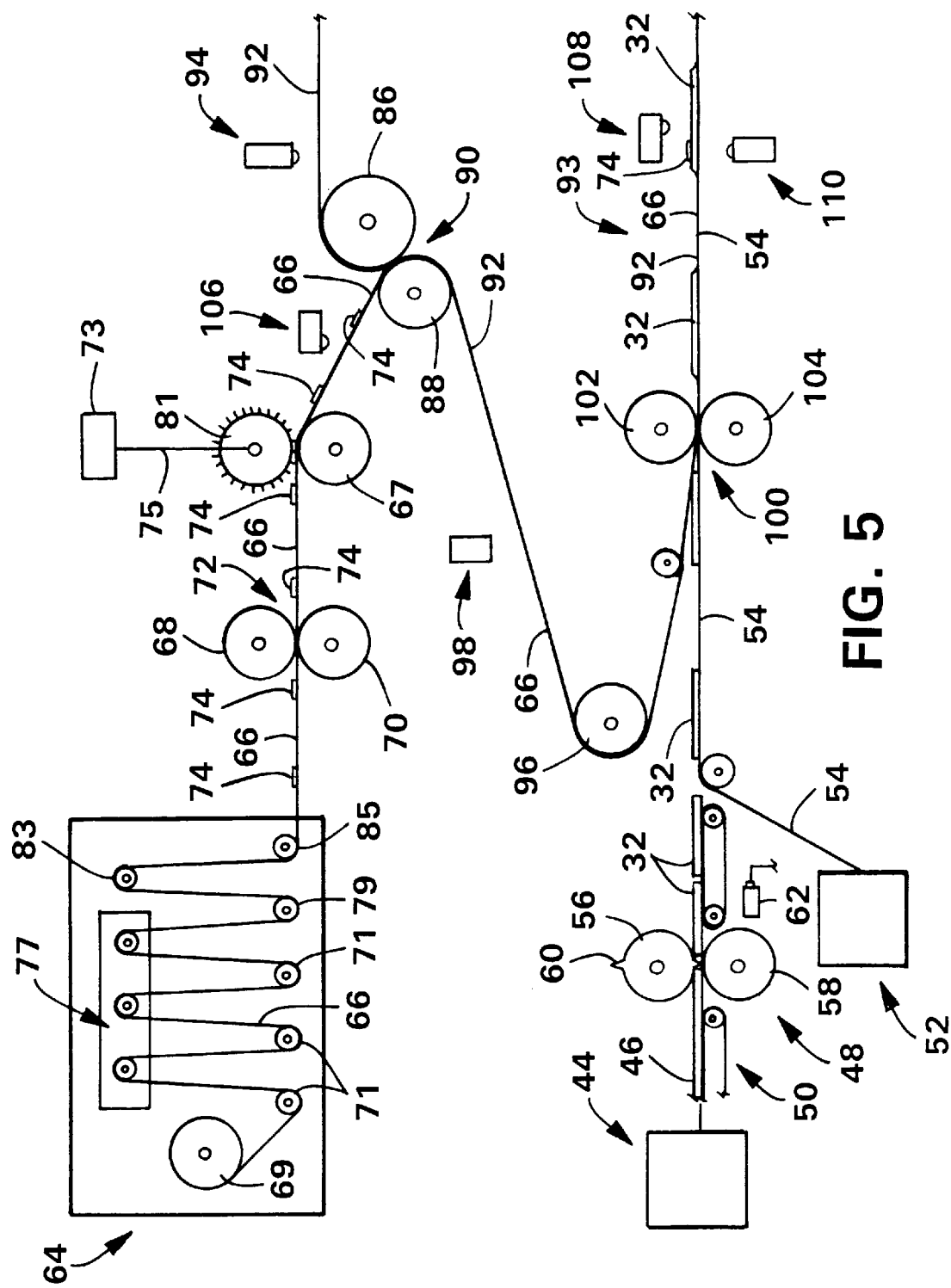
FIG. 5 schematically illustrates an apparatus and process for the manufacture of an article having a registered graphic thereon.

Referring now to FIG. 5, there is schematically shown an apparatus and process for assembling in part a plurality of training pants. A supply means 44 continuously supplies a continuous, tissue-wrapped absorbent 46 to a separating means 48 that separates the continuous, tissue-wrapped absorbent 46 into a plurality of distinct and separate absorbent pads 32. The supply means 44 can be any conventional mechanism for supplying the absorbent 46. Generally, a conventional supply means 44 will include a hammermill for forming fluff fibers and, if desired, for providing an enclosure for mixing superabsorbent material with the fluff fibers, and then depositing the fluff and superabsorbent material on a forming drum having a desired absorbent design. The forming drum then deposits the shaped absorbent on a continuously moving tissue material, which is thereafter delivered to a folding board for folding the issue about the absorbent. This provides the continuous, tissue-wrapped absorbent 46. The absorbent can include any desired mixture or blend of absorbing materials, such as fluff and superabsorbent materials. Suitable superabsorbent materials are available from various commercial vendors such as Dow Chemical Company, Hoechst-Celanese Corporation and Allied Colloids, Inc. Typically, a superabsorbent material is capable of absorbing at least about 15 times its weight in water, and desirably more than about 25 times its weight in water. A preferred fluff is that identified with the trade designation CR1654, available from Kimberly-Clark Corporation, Neenah, Wis., and is a bleached, highly absorbent sulfate wood pulp containing primarily soft wood fibers.

A conveyor means 50, which can be any conventional conveyor means well known in the art, conveys the absorbent 46 to the separating means 48. A supply means 52 provides a continuously moving first layer of material 54, upon which can be disposed any desired component, such as the separate and distinct absorbent pads 32 formed by separating means 48. The supply means 52 can be any standard unwind mechanism that generally comprises a pair of spindles, a festoon assembly, and a dancer roll for providing first layer 54 at a desired speed and tension. One example of a standard unwind is a model MB 820, available from Martin Automatic Corporation of Rockford, Ill. The continuously moving first layer of material 54 can be any desired material suitable for the particular product being assembled. In this description of a training pant 10 (FIG. 1), continuously moving first layer 54 is a liquid permeable material that will subsequently form or become liquid permeable topsheet 36 (FIG. 1). Topsheet 36 can be made of any suitable materials well known in the art, and examples of suitable materials are described in the aforementioned incorporated U.S. patents.

Upon being moved or delivered to separating means 48, the continuous, tissue-wrapped absorbent 46 is cut into the separate and distinct absorbent pads by a knife roll 56 and an anvil roll 58 comprising separating means 48. The knife roll 56 can have any desired number of blades thereon, and in this example has two blades 60 diametrically disposed thereon for forming absorbent pads 32. Knife roll 56 is driven by and mechanically coupled through gearing to anvil roll 58, which is operatively driven by a main lineshaft 128 (FIG. 6) in any suitable manner well known in the art. A constant reference means, such as a proximity switch 62, is coupled to anvil roll 58 for generating a reference signal for each cut absorbent pad 32. For purposes herein, the separating means 48 is operated at a substantially constant speed during the manufacturing process so that each reference signal generated by proximity switch 62 is considered a machine constant reference signal for purposes of comparison to other signals hereafter described. The machine-generated constant reference signal from proximity switch 62 is transmitted to a main control system for further processing as described hereafter.

The distinct and separate absorbent pads 32 formed by separating means 48 are selectively positioned upon the continuously moving first layer of material 54 provided by supply means 52. It is well known in the art to separate and selectively position individually cut absorbent pads onto a continuously moving layer, and any such suitable mechanism can be utilized herein.

A supply means 64, which can be a standard unwind similar to that used with reference to the supply means 52, provides a continuously moving second layer 66 of material that will subsequently be joined to continuously moving first layer 54. Supply means 64 comprises a center driven unwind spindle 69, a plurality of stationary rolls 71, an air dancer assembly 77, a driven feed roll 79, a dancer roll 83, and a stationary roll 85. Supply means 64 operates in a conventional manner well known in the art, in which air dancer assembly 77 provides festooning for splicing layers and a speed input signal for center driven unwind spindle 69, as well as dancer roll 83 providing a speed input signal to driven feed roll 79. Continuously moving second layer 66 is moved toward a pair of rolls comprising a drive roll 68 and a support roll 70 that form therebetween a feed nip 72. Drive roll 68 can be driven by any suitable motor, such as those described in the U.S. patents incorporated by reference herein. A suitable feed nip motor is a HR 2000 brushless AC servo motor available from Reliance Electric Company, of Cleveland, Ohio. The material of which second layer 66 is made is gatherable and elongatable, in that it can be gathered or elongated, by way of example only, between about 0.5% to about 5.0% of a length, for example, a machine product repeat length. In being elongatable, the material of which second layer 66 is made has the property of being thinned or stretched by breaking bonds within the layer when elongated. This thinning refers to the material's thickness, rather than to its length or width. Other materials having greater or lesser gathering and elongation can be utilized as the material or materials for second layer 66. The continuously moving second layer 66, in this particular description, is a liquid impermeable film that will subsequently form liquid impermeable outer cover 34 (FIG. 1), and such films are available from Edison Plastics Company of South Plainfield, N.J.

It is desired that the feed nip motor 148 (FIG. 6) and its drive system, which operates drive roll 68, is one that is capable of performing two types of controllable speed adjustments or variations, as controlled by the main control system, which will be described in greater detail hereafter. One speed adjustment or variation is to increase a present speed of the rotation to a faster speed of rotation, or to decrease a present speed of rotation to a slower speed of rotation. The other speed adjustment or variation is a momentary speed adjustment or variation comprising an incremental advance phase move, which is a momentary speed increase of drive roll 68 to provide a measured increased amount of the layer of material, or an incremental retard phase move, which is a momentary speed decrease of drive roll 68 to provide a measured decreased amount of the layer of material. The term "momentary speed increase" refers to increasing a first speed to a higher second speed for a selected period of time, and then causing the speed to return to the first speed, in order to advance the position of the layer and the associated graphics upstream of the nip by a measured amount. The term "momentary speed decrease" refers to decreasing a first speed to a lower second speed for a selected period of time, and then causing the speed to return to the first speed, in order to retard the position of the layer and the associated graphics upstream of the nip by a measured amount.

The present invention can be utilized to register two continuously moving layers together, so that a reference mark and/or component of one layer is registered with a reference mark and/or component on the second layer. In this particular description, a component, such as a registered graphic 38 (FIG. 1) on continuously moving second layer 66 (FIG. 5) is brought in registration with a component, such as an absorbent pad 32, on continuously moving first layer 54. By controllably registering a registered graphic 38 with an absorbent pad 32, the desired position of registered graphic 38 on a front panel 12 (FIG. 1) of a training pant 10 can be accomplished. An important function of a registered graphic 38 on a front panel 12 is that it visually informs the user of the proper orientation of the training pant 10 for donning purposes, thereby permitting the training pant to properly function, i.e., absorb waste, among other functions. The continuously moving layer 66 has, by way of example, preprinted thereon a plurality of separate and distinct graphics 38, such that the graphics 38 can be registered with the separate and distinct absorbent pads 32 on continuously moving layer 54. There is associated with each graphic 38 a preprinted reference mark 74, which in this case is an optical brightener. The graphics 38 and their respective reference marks 74 can be provided on layer 66 in any suitable manner well known in the art.

With reference to FIG. 3, there is illustrated a portion of continuously moving layer 66 having a plurality of the graphics 38 and reference marks 74 preprinted or prepositioned thereon. Associated with each graphic 38 is a printed waistband 76 with a printed front edge 78 and a printed back edge 80. Similarly, each reference mark 74 has a reference front edge 82 and a reference back edge 84. Each reference mark 74 will be used to properly position an associated graphic 38 with an absorbent pad 32. The reference marks 74 are positioned off graphics 38, but could be printed directly on the graphics 38 so as to be within the design of the graphics. Furthermore, the reference marks 74 can be eliminated, and a portion of a graphic 38 can be used as the reference mark. Detectable marks or the like also could be printed as part of graphics 38 and thereafter used for properly registering the graphics 38. However, for purposes of explanation and manufacture, reference marks 74 are provided a selected distance apart from respective graphics 38.

In the following description, the continuously moving second layer 66 will be described, by way of example, as being joined or laminated to another third layer 92 (FIG. 5) of material in order to produce a two-layered laminate that ultimately will form the liquid impermeable outer cover 34 (FIG. 1). The polyethylene film material of which layer 66 is made serves as a liquid impermeable barrier, while the third layer of material joined to layer 66 will provide cloth-like texture to the outer cover. The cloth-like layer will be the outermost layer. There is no requirement, however, for the third layer, and in some product designs, the cloth-like layer can be eliminated.

From supply means 64, layer 66 moves through the feed nip 72 formed by rolls 68 and 70 and toward an impresser or embosser mechanism or means, such as a variable impresser or embosser 65, with an impresser roll 81 and an associated receiving roll 67 operatively coupled thereto. The receiving roll 67 can be a recessed roll having a plurality of complementary recesses on its cylindrical outer surface. The impresser roll 81 of variable impresser 65 is moveable toward and away from receiving roll 67 by any suitable control means, such as a driven piston-cylinder arrangement, servo motor arrangement, or the like. One such example is a linear actuator 73 operatively connected by a connecting rod 75 to an impresser roll 81. Impresser roll 81 can comprise a plurality of projections extending outwardly from its cylindrical outer surface. These projections, in this embodiment, are a plurality of spaced-apart, discrete elongate flange members oriented generally parallel to the axis of impresser roll 81. These flange members and recesses in receiving roll 67 are complementary in that each flange member fits or nests in a respective recess. Impresser roll 81 and receiving roll 67 are operatively coupled together to provide this complementary fit or nesting. Other design projections and recesses are contemplated by the present invention, and include, but are not limited to, cylindrical or conical shapes, intersecting flange members, a plurality of flange members, in any desired geometrical or non-geometrical pattern, or combinations thereof.

One purpose of variable impresser or embosser 65 is to treat, when necessary, layer 66 to decrease the distance between reference marks 74. This can be accomplished by controllably moving impresser roll 81 against layer 66 through the controlled operation of linear actuator 73 and connecting rod 75. By controlling the movement of impresser roll 81 against layer 66, the pressure exerted by the flange members of impresser roll 81 against layer 66 can be controllably adjusted to, by way of example, pleat layer 66, thereby gathering it to decrease the distance between reference marks 74. Furthermore, the speed of drive roll 68 can be controllably adjusted or varied by motor 148 (FIG. 6) in order to selectively change the thickness of layer 66. For example, the speed of drive roll 68 needs to be increased to decrease the tension on layer 66 downstream of, or beyond, drive roll 68, thereby causing a slight contraction of layer 66 and a slight increase in its thickness to facilitate the pleating. In addition to pleating to decrease this distance, other methods include, but are not limited to, crimping, radiation treatment, chemical treatment, corrugating, elasticizing, ultrasonic bonding, or the like. If, however, layer 66 is determined not to need a decrease in distance between reference marks 74, layer 66 will move through variable impresser 65 without being treated, since impresser roll 81 will have been controllably moved in a direction away from receiving roll 67 to present a clear or unobstructed path therebetween.

Another purpose of variable impresser 65 is to treat, when necessary, layer 66 to increase the distance between reference marks 74. This can be accomplished by controllably moving impresser roll 81 against layer 66 through the controlled operation of linear actuator 73 and connecting rod 75. By controlling the movement of impresser roll 81 against layer 66, the pressure exerted by the flange members of impresser roll 81 against layer 66 can be controllably adjusted to, by way of example, slit or weaken layer 66, thereby elongating it to increase the distance between reference marks 74. Furthermore, the speed of drive roll 68 can be controllably adjusted or varied by motor 148 (FIG. 6) in order to selectively change the thickness of layer 66. For example, the speed of drive roll 68 may need to be decreased to increase the tension on layer 66, thereby causing a slight elongation of layer 66 and a slight decrease or thinning in its thickness. In addition to slitting to increase the distance, other methods include, but are not limited to, nipping, calendering, chemical treatment, aperturing, radiation treatment, scoring, cold rolling or the like. If, however, layer 66 is determined not to need an increase in distance between reference marks 74, layer 66 will move through impresser 65 without being treated, since impresser roll 81 will have been controllably moved in a direction away from receiving roll 67 to present a clear or unobstructed path therebetween.

After variable impresser 65, layer 66 is driven or moved toward a laminator chill roll 86 and an associated support roll 88, which form therebetween a laminator nip 90. A continuously moving layer 92 is provided and driven in any suitable manner to laminator chill roll 86. An adhesive applicator 94 applies a desired pattern of a suitable adhesive to the continuously moving layer 92. In this particular embodiment, layer 92 is a nonwoven web, such as a spunbond polypropylene web having a basis weight of about 20 grams per square meter (gsm). The adhesive applicator 94 can be any suitable applicator well known in the art that can provide or apply the desired pattern of adhesive. The adhesive used can be any suitable adhesive that is compatible to layers 66 and 92, in order to ensure their proper lamination together. Continuously moving layer 92 can be provided by a supply means (not shown) similar to supply means 52 and 64.

Laminator chill roll 86 is driven by the lineshaft 128 (FIG. 6) and assists in moving the layers in the process. The laminator chill roll 86 also serves to cool the adhesive applied by adhesive applicator 94 for processing purposes, thereby preventing adhesives from bleeding through the layers 66 or 92.

Once layers 66, 92 are laminated and pass through laminator nip 90, they are continuously moved to a construction chill roll 96, and have an adhesive applied to the outermost surface of layer 66. Construction chill roll 96 is also driven by lineshaft 128. The adhesive applied by adhesive applicator 98 will ultimately join layers 66, 92 to continuously moving first layer 54. Thus, adhesive applicator 98 is designed to apply the appropriate adhesive pattern and amount of adhesive to ensure the desired joining of the layers 66, 92, and 54. The construction adhesive applicator 98, as well as the adhesive applied thereby, can be any type of applicator suitable for the desired adhesive pattern, and appropriate and compatible for the materials to be joined.

From construction chill roll 96, the laminated layers 66, 92 are then superimposed over continuously moving layer 54, and together the layers pass through a product tacker 100 comprising a drive roll 102 driven by lineshaft 128 (FIG. 6) and a rubber-coated idler roll 104. Tacker 100 compresses the layers together in order to cause the applied adhesive to join layers 66, 92 to continuously moving layer 54, thereby forming a continuously moving composite layer 93 as illustrated in FIGS. 4 and 5.

Continuing to refer to FIG. 5, a first sensing means, such as a sensor 106, is suitably positioned between drive roll 68 and laminator chill roll 86 for sensing or detecting a reference mark 74 and generating a signal, i.e., a reference mark signal, in response to each reference mark 74. Optionally, sensor 106 could be located in close proximity to laminator chill roll 86, and either upstream or downstream of roll 86. Since the reference marks 74 are ultraviolet-sensitive optical brighteners, a suitable sensor is a SICK detector model LUT 2-6 available from SICK OPTIK ELEKTRONIK, Inc., having a business office in St. Paul, Minn.

Positioned downstream of product tacker 100 are second and third sensing means, such as a sensor 108 and a photoeye 110. Sensor 108 can be the same type of ultraviolet detector as sensor 106. The photoeye 110 is desirably a Banner RSBF scanner block, RPBT wiring base, IR 2.53S fiber-optic pair device, available from Banner Engineering, Corp. of Minneapolis, Minn. Photoeye 110 is designed to optically sense or detect a component, such as absorbent pad 32, and to generate an electrical signal in response thereto. In this particular description, both sensors 106 and 108 are designed to sense or detect, and generate a signal in response to a reference mark 74; and photoeye 110 is designed to sense or detect, and generate a signal in response to an absorbent pad 32. If desired, photoeye 110 can sense other components, such as waist elastics, leg elastics, fastening tapes utilized in diapers, or the like. A reference mark also can be associated with each absorbent pad 32 in the same manner that a reference mark 74 is associated with a graphic 38; and in this case, the pad photoeye 110 can be replaced with a sensor similar to sensors 106,108. Similarly, sensors 106, 108 can be replaced with other sensors, similar to photoeye 110, in order to optically sense or detect a component or other structure in order to generate an appropriate signal.

With reference to FIG. 4, there is illustrated a continuously moving composite layer 93 comprising layers 66, 92, and 54 (FIG. 5) after they have been joined together by product tacker 100. Each printed waistband 76 will ultimately be cut along a respective cut line 120 in order to form individual products. In FIG. 4, once cut lines 120 have been separated, a front waist edge 116 and a back waist edge 118 are formed for each assembled product. One of the important features in FIG. 4 is the relative placement of a graphic 38 with respect to each product that will eventually be formed. Each graphic 38 is located in the front panel 12 (FIG. 1) and is located in the same position relative to an absorbent pad front edge 112 (FIG. 4). Naturally, other marks or product components can be in registration with other different reference marks or product components. For example, a simulated waist ruffle 29 (FIG. 2) can be registered relative to a waist opening, or leg elastics, such as leg elastics 30 (FIG. 1), can be desirably registered in relation to an absorbent pad, such as absorbent pad 32 (FIG. 4).

Figure 6:
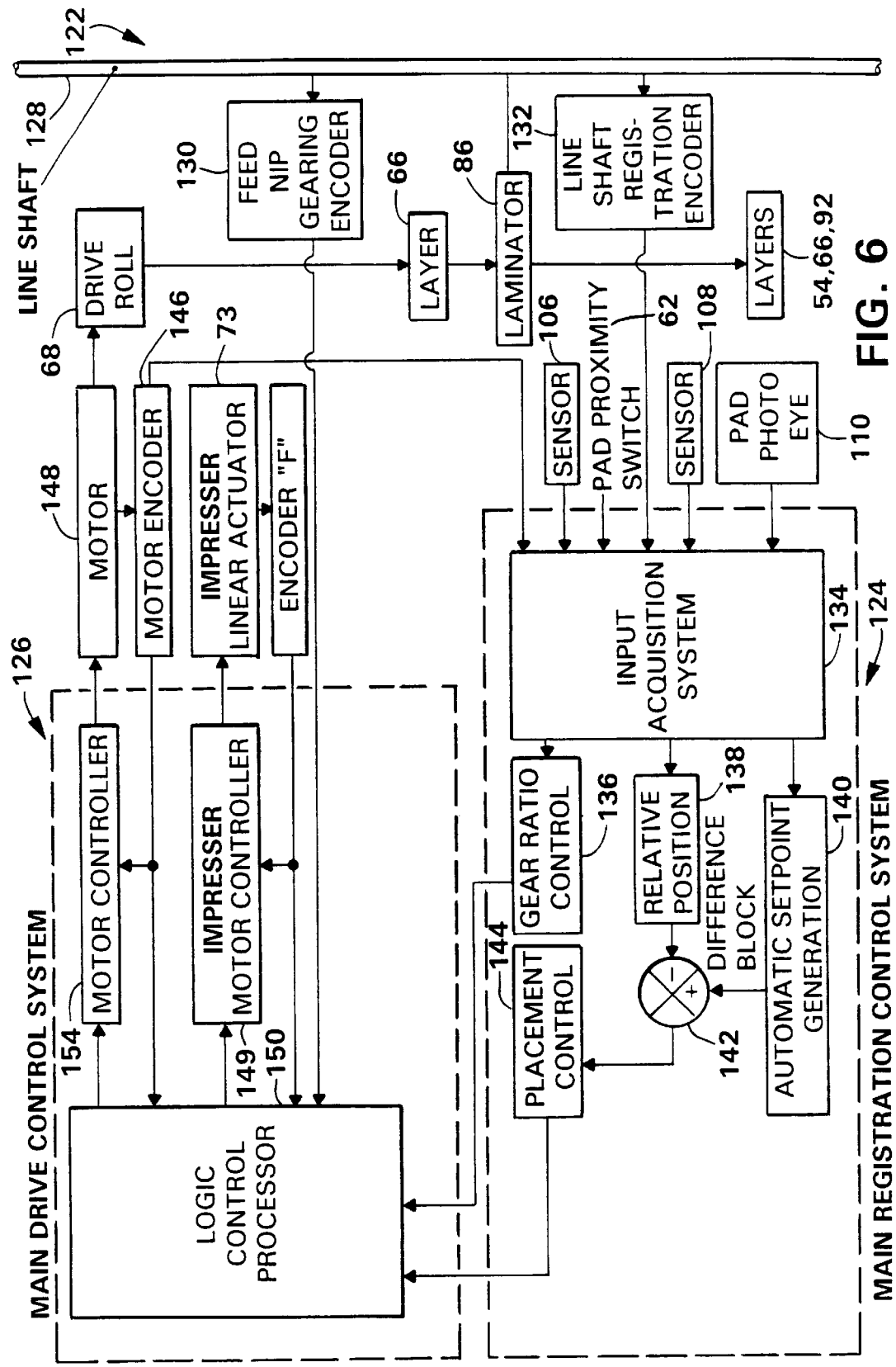
FIG. 6 illustrates a schematic block diagram of the flow of data utilized in conjunction with the apparatus and process in FIG. 5.

Referring to FIG. 6, there is schematically illustrated a main control system with a mechanical side 122. The main control system comprises a main registration control system 124 that receives various generated signals, processes them in accordance with programmed instructions, and generates output signals to a main drive control system 126. The main drive control system 126 receives the signals from the main registration control system 124, and in response thereto operates, as necessary, variable impresser 65 and drive roll 68.

Main drive control system 126 can be designed to operate or control other areas or mechanisms; for example, it is desired that the impresser roll 81 is suitably coupled to the drive roll 68 such that it is driven at relatively the same speed.

Mechanical side 122 comprises a main lineshaft 128 that directly drives selected mechanisms or, through a system of gears and other coupling devices, both electrical and mechanical, indirectly drives other mechanisms. Lineshaft 128 is driven at a constant speed, by any suitable means known in the art, and those mechanisms driven by lineshaft 128 are also driven at a constant speed, which may or may not be the same speed as that of lineshaft 128. Specifically, a feed nip gearing encoder 130 and a lineshaft registration encoder 132 are operatively coupled to lineshaft 128. Examples of encoders include an H25D-SS-2500-ABZC-8830-LED-SM18 (which can be used as encoder 130), available from BEI Motor System, Co. of Carlsbad, Calif., and a 63-P-MEF-1000-T-0-00 (which can be encoder 132) available from Dynapar Corp. of Gurnee, Ill. Feed nip gearing encoder 130 is operatively coupled to lineshaft 128 to rotate at a constant speed, such that four revolutions of encoder 130 represents one machine product repeat length.

The main registration control system 124 comprises hardware and/or preprogrammed software instructions, and can be represented, with reference to FIG. 6, as comprising an input acquisition system 134, a gear ratio control 136, a relative position 138, an automatic set point generation 140, a difference block 142, and a placement control 144. The main registration control system 124 includes a computer, which can comprise, for example, a VME-based microprocessor, such as a SYS68K/CPU-40B/4-01 available from Force Computers, Inc. of Campbell, Calif.

As illustrated in FIG. 6, input acquisition system 134 can be designed to receive the following six generated signals: (i) a signal from a motor encoder 146 operatively coupled to a motor 148 that drives drive roll 68, (ii) a signal from sensor 106 (FIG. 5), (iii) a signal from proximity switch 62 (FIG. 5), (iv) a signal from lineshaft registration encoder 132, (v) a signal from sensor 108 (FIG. 5), and (vi) a signal from photoeye 110 (FIG. 5). Input acquisition system 134 receives and counts the pulses generated by motor encoder 146 and lineshaft registration encoder 132, and receives signals from sensors 106, 108, proximity switch 62, and photoeye 110. Referencing the accumulated counts of encoder 146 and the accumulated counts of encoder 132, input acquisition system 134 performs preprogrammed instructions that are specific to the respective received signals, and stores the results of the instructions.

For the gear ratio control 136, a signal counter in input acquisition system 134 counts the pulses from motor encoder 146, and receives signals from sensor 106 in response to each reference mark 74 (FIG. 5). The input acquisition system 134 then measures the counted pulses representing a distance between every two successive reference marks 74, and performs a running average of those measured counts. The term "running average" refers to averaging the same number of data; for example, for each newly received datum input, the oldest datum is removed from the averaging calculation. The averaging of the counts between two successive reference marks 74 creates an average measurement upon which the next gear ratio value will be derived by gear ratio control 136, as opposed to basing a control decision on the measurement from just one pair of reference marks 74. This averaging "smoothes out" the measurements, and is necessitated due to the variability of the apparatus and process. The number of measurements to average is controllable, and is set or determined by providing an appropriate instruction via manual input in any suitable manner well known in the art. In conjunction with performing a running average of the measured counts, the input acquisition system 134 performs a filtering function, which is preprogrammed, to filter out signal anomalies. Examples of such signal anomalies include a dirty photoeye, missing or extra reference marks 74, movement or weaving of the layers, measuring the counts outside a preprogrammed range for averaging purposes, known inaccurate data due to registration control events, or the like.

For the relative position 138, the input acquisition system 134 counts the pulses received from lineshaft registration encoder 132, and receives signals generated by sensor 106 and proximity switch 62. Input acquisition system 134 then determines and records the current accumulated number of pulses upon receiving a signal from sensor 106, and determines and records the current accumulated number of pulses upon receiving a signal from proximity switch 62.

For the automatic set point generation 140, input acquisition system 134 counts the pulses received from lineshaft registration encoder 132, and receives the signals generated by sensor 108 and photoeye 110. It then determines and records the current accumulated number of pulses upon receiving a signal from sensor 108, and determines and records the current accumulated number of pulses upon receiving a signal from photoeye 110. Thereafter, input acquisition system 134 calculates the difference between the current accumulated number of pulses from one signal of sensor 108 and the current accumulated number of pulses from an associated signal of photoeye 110; the "associated signal" refers to the signal generated by photoeye 110 (FIG. 5), with the signal from sensor 108, for each machine product repeat length. With these calculated differences, input acquisition system 134 performs a running average and standard deviation for those differences.

The various calculations and functions performed by input acquisition system 134 are utilized by other portions of main registration control system 124 in order to generate commands to main drive control system 126 (FIG. 6), which generally comprises a logic/control processor 150, a nip motor controller 154, and an impresser motor controller 149. The main drive control system 126 includes a computer, which can comprise, for example, a Reliance Distributed Control System made by Reliance Electric, Co. The Distributed Control System includes a Reliance Electric Automax Processor and associated hardware.

The gear ratio control 136 queries the input acquisition system 134 every 20 products, i.e., every 20 machine product repeat lengths, for the current running average of measured counts representing a distance between successive reference marks 74 (FIG. 5), which is the repeat value. The number of product lengths determining a query from gear ratio control 136 is adjustable, and can be changed manually by the operator. After determining the repeat value, gear ratio control 136 performs a gear ratio calculation in accordance with preprogrammed instructions to determine a new gear ratio value, if necessary. That new gear ratio value is then transmitted to the logic control processor 150 of main drive control system 126. The gear ratio value is calculated by dividing the repeat value by the number of encoder counts from the feed nip gearing encoder 130 (FIG. 6) that occur in one machine product repeat length. The purpose of this is to accommodate the repeat of reference marks without comparing to a target value.

The relative position 138 of main registration control system 124 queries input acquisition system 134 for the current accumulated number of pulses relative to sensor 106, and the current accumulated number of pulses relative to proximity switch 62. Relative position 138 then determines the difference between the two current accumulated number of pulses in order to calculate a relative position of a reference mark 74 (FIG. 5) to the associated proximity switch signal for that specific query for each machine product repeat length. The relative position 138 then generates and transmits to difference block 142 a relative position value.

The automatic set point generation 140 queries the input acquisition system 134 for each machine product repeat length representing a single product. The occurrence of each product, or machine product repeat length, is determined from the lineshaft registration encoder 132, in which two revolutions of lineshaft registration encoder 132 is equivalent to one product length. In this particular example, two revolutions of lineshaft registration encoder 132 is 2,000 counts. The input acquisition system 134 responds to each query from automatic set point generation 140 with the current running average and standard deviation of the difference calculated between the current accumulated number of pulses for one signal of sensor 108 and the current accumulated number of pulses from an associated signal from pad photoeye 110 for each product; the current running average of this calculation is the actual position value. The automatic set point generation 140 then compares a standard deviation with a preset limit, which has been manually entered, and if the standard deviation is outside the preset limit, the automatic set point generation 140 will ignore that datum and not determine a new set point since the standard deviation data is considered too variable to make an accurate set point adjustment. If the standard deviation is within the preset limit, the automatic set point generation 140 will then determine the difference between the actual position value and a manually entered target value, which is the desired actual position value. If the new calculated difference is determined, by automatic set point generation 140, to be within a prescribed range, no further action or calculation will be made. However, if the difference is outside the prescribed range, the automatic set point generation 140 will determine a new control set point. This new control set point is derived by adding to the current set point the difference between the target value and actual position value.

Once every machine product repeat length, a difference block 142 determines the difference between the current control set point value from automatic set point generation 140 and the associated relative position value from relative position 138, which is the placement error. The difference block 142 transmits this placement error, in lineshaft encoder counts, to placement control 144. The placement control 144 compares the placement error to a tolerance band 170 (FIG. 7), which defines an acceptable deviation of the relative position value about the current control set point. The tolerance band 170 remains constant about the control set point, but the control set point can vary as calculated by automatic set point generation 140. As a result, while the position control of the reference marks occurs at nip 72, the set point for this position control is accurately derived from the signals generated by sensor 108 and photoeye 110.

Figure 7:
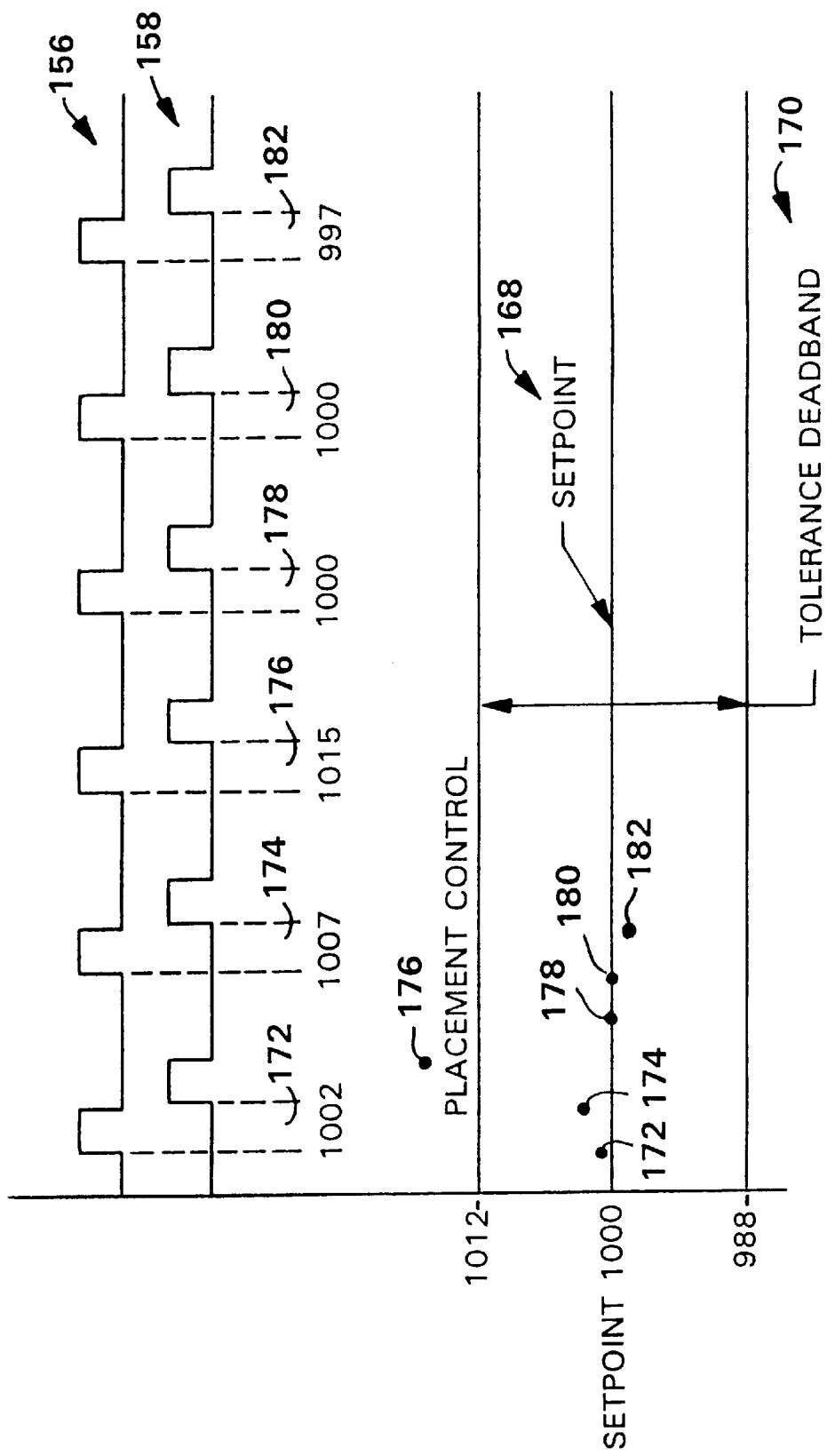
FIG. 7 graphically illustrates a placement control utilized in conjunction with the apparatus and process in FIG. 5.

With reference to FIG. 7, there is illustrated one derived set point 168 having a prescribed tolerance band 170. For purposes of explanation, the control set point 168 has a value of 1,000 counts, and the tolerance band 170 represents a deviation of plus or minus 12 counts. Each of the datum points 172,174, 176, 178,180 and 182, represents one product's relative position value as calculated by relative position 138. Waveform 156 represents signals generated by proximity switch 62 (FIG. 6), and waveform 158 represents signals generated by sensor 106 (FIG. 6). If a placement error value remains within tolerance band 170, no placement command will be generated. However, if a placement error value is outside tolerance band 170, then placement control 144 (FIG. 6) will generate a placement command. The placement command is directly proportional to the size of the difference represented by the value from difference block 142 and calls for a measured advance or retard in the position of layer 66. The generated placement command is then transmitted to the logic/control processor 150 of main drive control system 126. FIG. 7 illustrates an example of how placement control 144 (FIG. 6) compares each datum point 172–182 to a current control set point in order to generate a placement error. The placement error for each datum point is compared to tolerance band 170 to determine if a placement command should be generated. In the example, point 176 is the only datum point where the placement error falls outside the tolerance band 170, which causes a placement command to be generated, thereby causing a following datum point to fall within the tolerance band 170.

The logic control processor 150 (FIG. 6) of main drive control system 126 searches for and receives new commands or signals from main registration control system 124. Specifically, processor 150 searches for and receives gear ratio commands or signals, and placement commands or signals from main registration control system 124. The gear ratio commands or signals and placement commands or signals are used in accordance with preprogrammed instructions to transmit a command or signal to the nip motor controller 154 and to impresser motor controller 149.

Upon receiving a gear ratio command from the main registration control system 124, the logic control processor 150 will send a speed command to the nip motor controller 154 which controls the speed of drive roll 68. The gear ratio command will be simultaneously compared to predetermined limits based on material characteristics of layer 66. If the gear ratio is above or below the pre-determined limits, the impresser will be engaged until the gear ratio is within the limits.

Upon receiving a placement command from the main registration control system 124, the logic control processor 150 will send a momentary speed command to the nip motor controller 154 which controls the speed of drive roll 68. Since the placement corrections are generally larger than the material can handle within its elastic range, the impresser is always engaged during a placement correction. The placement command will be limited to a maximum value determined by the material's ability to be gathered or elongated by the impresser. After each placement correction the main registration control system will gather data and calculate if an additional placement correction is required.

Upon receiving a gear ratio command from the main registration control system 124, the logic control processor 150 will send a speed command to the nip motor controller 154 which controls the speed of drive roll 68. The gear ratio command will be simultaneously compared to predetermined limits based on material characteristics of layer 66. If the gear ratio is above or below the predetermined limits, the impresser will be engaged until the gear ratio is within the limits.

When the logic control processor 150 engages the impresser, it sends a signal to the impresser motor controller 149 to operate the motor of linear actuator 73. Linear actuator 73 then drives, via connecting rod 75, impresser roll 81 against layer 66 to apply a selected pressure for a predetermined period of time necessary to gather or elongate layer 66. At the end of this predetermined period of time, main drive control system 126 will cause linear actuator 73 to withdraw impresser roll 81 from layer 66.

Logic control processor 150 precisely links the speed of the poly nip drive motor 148 to the speed of the lineshaft 128 through an electronically changeable gear ratio in accordance with preprogrammed instructions. This effectively synchronizes the speed of the nip motor 148 to the lineshaft 128 and allows frequent changes to the gear ratio, and thus the speed of motor 148. These changes in speed of motor 148, and thus drive roll 68 and impresser roll 81, which are suitably coupled together, are desirable to accommodate the gathering or elongating of layer 66.

As described, this results in the desired registration of graphic 38 (FIG. 1) or graphic 42 (FIG. 2) in respective training pants 10, 40. By selectively controlling the distance between successive reference marks 74 (FIG. 5), each mark 74 can be respectively registered with an associated or corresponding component, such as an absorbent pad 32. Controlling the distance between reference marks 74 to a selected distance, such as machine product repeat length, accommodates or corrects for variations or other types of anomalies that may be present in the apparatus or process. By adjusting the gathering or elongating of continuously moving second layer 66, using impressing in conjunction with the tension on layer 66, it can be appropriately registered with continuously moving first layer 54, thereby ensuring proper registration of a desired component, such as a graphic 38, to another component, such as a front panel 12 (FIG. 1).

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and fall within the limits of the appended claims.

What is claimed is:

1. A process for controllably registering a plurality of components of a continuously moving first layer with a plurality of components on a continuously moving second layer, comprising the steps of:

providing a continuously moving first layer including a plurality of components, providing a continuously moving second layer including a plurality of components, representing the components of one of the continuously moving layers with a respective plurality of reference marks, sensing each of the reference marks and generating a reference mark signal in response thereto, measuring the distance between two successive reference mark signals and generating a repeat corrective control signal in accordance with preprogrammed instructions, selectively applying pressure to the continuously moving one layer in response to a generated repeat corrective control signal to adjust the distance between two successive reference marks, superimposing the continuously moving first layer and the continuously moving second layer together, sensing a reference mark and its corresponding component of the other layer, and generating a placement corrective control signal in accordance with preprogrammed instructions, and adjusting the speed of the continuously moving one layer in response to a generated placement corrective control signal to controllably register a reference mark on the continuously moving one layer with its corresponding component on the continuously moving other layer.

2. The process of claim 1 wherein the step of generating a repeat corrective control signal includes generating a gathering repeat corrective control signal, and wherein the step of selectively applying pressure includes gathering the one layer.

3. The process of claim 1 wherein the step of generating a repeat corrective control signal includes generating an elongating repeat corrective control signal, and wherein the step of selectively applying pressure includes elongating the one layer.

4. The process of claim 2 wherein the step of gathering includes pleating the one layer.

5. The process of claim 3 wherein the step of elongating includes thinning the one layer.

6. The process of claim 1 wherein the components of the one layer are spaced apart a distance substantially the same as a machine product repeat length, and the components of the other layer are spaced apart a distance substantially the same as the machine product repeat length.

7. A process for controllably registering a plurality of reference marks of a continuously moving first layer with a plurality of corresponding reference marks of a continuously moving second layer, comprising the steps of:

providing a continuously moving first layer including a plurality of reference marks selectively positioned thereon, providing a continuously moving second layer including a plurality of corresponding reference marks selectively positioned thereon, sensing each of the reference marks of one of the continuously moving layers and generating a reference mark signal in response thereto, measuring the distance between two successive reference mark signals and generating a repeat corrective control signal in accordance with preprogrammed instructions, impressing the continuously moving one layer in response to a generated repeat corrective control signal, superimposing the continuously moving layers together, sensing a reference mark of the continuously moving one layer and its corresponding reference mark of the continuously moving other layer and generating a placement corrective control signal in accordance with preprogrammed instructions, and adjusting the speed of the continuously moving one layer in response to a generated placement corrective control signal to controllably register a reference mark of the continuously moving one layer with its corresponding reference mark on the continuously moving other layer.

8. The process of claim 7 wherein the step of generating a repeat corrective control signal in accordance with preprogrammed instructions includes generating a gathering repeat corrective control signal or an elongating repeat corrective control signal, and wherein the step of impressing the continuously moving one layer includes decreasing the tension on the continuously moving one layer in response to a gathering repeat corrective control signal, or increasing the tension on the continuously moving one layer in response to an elongating repeat corrective control signal.

9. The process of claim 8 wherein the step of decreasing the tension includes increasing the thickness of the continuously moving one layer.

10. The process of claim 8 wherein the step of increasing the tension includes decreasing the thickness of the continuously moving one layer.

11. The process of claim 8 wherein the reference marks of the first layer are spaced apart a selected distance, and wherein the reference marks of the second layer are spaced apart a selected distance.

12. The process of claim 11 wherein the reference marks of the first layer are spaced apart a distance substantially the same as the machine product repeat length, and wherein the reference marks of the second layer are spaced apart a distance substantially the same as the machine product repeat length.

13. An apparatus for controllably registering a plurality of components of a continuously moving first layer with a plurality of components on a continuously moving second layer, comprising:

means for providing a continuously moving first layer including a plurality of components, means for providing a continuously moving second layer including a plurality of components being represented with a respective plurality of reference marks, means for sensing each of the reference marks, and means for generating a reference mark signal in response thereto, means for measuring the distance between the two successive reference mark signals, and means for generating a repeat corrective control signal in accordance with preprogrammed instructions, means for selectively applying pressure to the continuously moving one layer in response to a generated repeat corrective control signal to adjust the distance between two successive reference marks, means for superimposing the continuously moving first layer and the continuously moving second layer together, means for sensing a reference mark and its corresponding component of the first layer, and means for generating a placement corrective control signal in accordance with preprogrammed instructions, and means for adjusting the speed of the continuously moving second layer in response to a generated placement corrective control signal to controllably register a reference mark on the continuously moving second layer with its corresponding component on the continuously moving first layer.

14. The apparatus of claim 13 wherein the means for generating a repeat corrective control signal generates a gathering repeat corrective control signal, and wherein the means for selectively applying pressure includes means for gathering the second layer.

15. The apparatus of claim 13 wherein the means for generating a repeat corrective control signal generates an elongating repeat corrective control signal, and wherein the means for selectively applying pressure includes means for elongating the second layer.

16. The apparatus of claim 14 wherein the means for gathering includes means for pleating the second layer.

17. The apparatus of claim 15 wherein the means for elongating includes means for thinning the second layer.

18. The apparatus of claim 13 wherein the components of the second layer are spaced apart a distance substantially the same as a machine product repeat length, and the components of the first layer are spaced apart a distance substantially the same as the machine product repeat length.

19. An apparatus for controllably registering a plurality of reference marks of a continuously moving first layer with a plurality of corresponding reference marks of a continuously moving second layer, comprising:

means for providing a continuously moving first layer including a plurality of reference marks selectively positioned thereon, means for providing a continuously moving second layer including a plurality of corresponding reference marks selectively positioned thereon, means for sensing each of the reference marks of one of the continuously moving layers and means for generating a reference mark signal in response thereto, means for measuring the distance between two successive reference mark signals and means for generating a repeat corrective control signal in accordance with preprogrammed instructions, means for impressing the continuously moving one layer in response to a generated repeat corrective control signal, means for superimposing the continuously moving layers together, means for sensing a reference mark of the continuously moving one layer and its corresponding reference mark of the continuously moving other layer, and means for generating a placement corrective control signal in accordance with preprogrammed instructions, and means for adjusting the speed of the continuously moving one layer in response to a generated placement corrective control signal to controllably register a reference mark of the continuously moving one layer with its corresponding reference mark on the continuously moving other layer.

20. The apparatus of claim 19 wherein the means for generating a repeat corrective control signal in accordance with preprogrammed instructions generates a gathering repeat corrective control signal or an elongating repeat corrective control signal, and wherein the means for impressing the continuously moving one layer includes means for decreasing the tension on the continuously moving one layer in response to a gathering repeat corrective control signal, and means for increasing the tension on the continuously moving one layer in response to an elongating repeat corrective control signal.

21. The apparatus of claim 20 wherein the means for decreasing the tension increases the thickness of the continuously moving one layer.

22. The apparatus of claim 20 wherein the means for increasing the tension decreases the thickness of the continuously moving one layer.

23. The apparatus of claim 20 wherein the reference marks of the first layer are spaced apart a selected distance, and wherein the reference marks of the second layer are spaced apart a selected distance.

24. The apparatus of claim 20 wherein the reference marks of the first layer are spaced apart a distance substantially the same as the machine product repeat length, and wherein the reference marks of the second layer are spaced apart a distance substantially the same as the machine product repeat length.

* * * * *